(12) United States Patent
Vardi et al.

(10) Patent No.: US 6,962,602 B2
(45) Date of Patent: Nov. 8, 2005

(54) METHOD FOR EMPLOYING AN EXTENDIBLE STENT APPARATUS

(76) Inventors: Gil M. Vardi, 333 E. Ontario, Apt. 1002-B, Chicago, IL (US) 60611; Charles J. Davidson, 1311 Sunview La., Winnetka, IL (US) 60093

(*) Notice: Subject to any disclaimer, the term of this patent is extended or adjusted under 35 U.S.C. 154(b) by 294 days.

(21) Appl. No.: 10/050,524

(22) Filed: Jan. 18, 2002

(65) Prior Publication Data

US 2002/0116047 A1 Aug. 22, 2002

Related U.S. Application Data

(60) Continuation of application No. 08/935,383, filed on Sep. 23, 1997, now abandoned, which is a division of application No. 08/744,002, filed on Nov. 4, 1996, now abandoned.

(51) Int. Cl.⁷ .................................................. A61F 2/06
(52) U.S. Cl. ...................... 623/1.11; 623/1.35; 606/108
(58) Field of Search ............................. 623/1.11, 1.12, 623/1.31, 1.34, 1.35; 606/108, 153, 155

(56) References Cited

U.S. PATENT DOCUMENTS

| | | |
|---|---|---|
| 1,596,754 A | 8/1926 | Moschelle |
| 3,657,744 A | 4/1972 | Ersek |
| 3,872,893 A | 3/1975 | Roberts |
| 4,140,126 A | 2/1979 | Choudhury |
| 4,309,994 A | 1/1982 | Grunwald |
| 4,410,476 A | 10/1983 | Redding et al. |
| 4,413,989 A | 11/1983 | Schjeldahl et al. |
| 4,421,810 A | 12/1983 | Rasmussen |
| 4,453,545 A | 6/1984 | Inoue |
| 4,503,569 A | 3/1985 | Dotter |
| 4,552,554 A | 11/1985 | Gould et al. |
| 4,681,570 A | 7/1987 | Dalton |
| 4,689,174 A | 8/1987 | Lupke |
| 4,731,055 A | 3/1988 | Melinyshyn et al. |
| 4,733,665 A | 3/1988 | Palmaz |
| 4,739,762 A | 4/1988 | Palmaz |
| 4,769,029 A | 9/1988 | Patel |
| 4,782,128 A | 12/1988 | Rosenbluth |
| 4,819,664 A | 4/1989 | Nazari |
| 4,872,874 A | 10/1989 | Taheri |
| 4,878,495 A | 11/1989 | Grayzel |
| 4,896,670 A | 1/1990 | Crittenden |
| 4,900,314 A | 2/1990 | Quackenbush |
| 4,906,244 A | 3/1990 | Pinchuk et al. |
| 4,909,258 A | 3/1990 | Kuntz et al. |
| 4,946,464 A | 8/1990 | Pevsner |
| 4,957,501 A | 9/1990 | Lahille et al. |
| 4,957,508 A | 9/1990 | Kaneko et al. |
| 4,964,850 A * | 10/1990 | Bouton et al. ............... 604/540 |
| 4,983,167 A | 1/1991 | Sahota |
| 4,994,071 A | 2/1991 | MacGregor |
| 5,042,976 A | 8/1991 | Ishitsu et al. |
| 5,054,501 A | 10/1991 | Chuttani et al. |
| 5,059,177 A | 10/1991 | Towne et al. |
| 5,061,240 A | 10/1991 | Cherian |
| 5,064,435 A | 11/1991 | Porter |
| 5,085,664 A | 2/1992 | Bozzo |
| 5,102,403 A | 4/1992 | Alt |

(Continued)

*Primary Examiner*—Paul B. Prebilic
(74) *Attorney, Agent, or Firm*—Patton Boggs LLP

(57) ABSTRACT

An imageable extendable stent apparatus for insertion into a bifurcating vessel or a vessel opening. The stent apparatus comprises a main stent and a flared stent, which may used individually or in combination with each other. The flared stent may be interlocked with the main stent to provide stent coverage over the entire region of a bifurcation. The main stent of the apparatus may be deployed at the bifurcation point of a vessel, allowing unimpeded future access to the side branch of the bifurcated vessel. The flared stent may be employed at vessel openings. Also disclosed and claimed are methods for implanting the extendable stent apparatus into the bifurcation point or the ostium of a subject vessel.

7 Claims, 5 Drawing Sheets

U.S. PATENT DOCUMENTS

| | | |
|---|---|---|
| 5,102,417 A | 4/1992 | Palmaz |
| 5,104,404 A | 4/1992 | Wolff |
| 5,117,831 A | 6/1992 | Jang |
| 5,122,125 A | 6/1992 | Deuss |
| 5,135,536 A | 8/1992 | Hillstead |
| 5,147,317 A | 9/1992 | Shank et al. |
| 5,159,920 A | 11/1992 | Condon et al. |
| 5,176,617 A | 1/1993 | Fischell et al. |
| 5,192,297 A | 3/1993 | Hull |
| 5,195,984 A | 3/1993 | Schatz |
| 5,211,683 A | 5/1993 | Maginot |
| 5,222,971 A | 6/1993 | Willard et al. |
| 6,217,440 B1 | 6/1993 | Frassica |
| 5,226,913 A | 7/1993 | Pinchuk |
| 5,234,457 A | 8/1993 | Andersen |
| 5,236,446 A | 8/1993 | Dumon |
| 5,257,974 A | 11/1993 | Cox |
| 5,263,932 A | 11/1993 | Jang |
| 5,282,472 A | 2/1994 | Companion et al. |
| 5,304,220 A | 4/1994 | Maginot |
| 5,320,605 A | 6/1994 | Sahota |
| 5,324,257 A | 6/1994 | Osborne et al. |
| 5,337,733 A | 8/1994 | Bauerfeind et al. |
| 5,338,300 A | 8/1994 | Cox |
| 5,342,295 A | 8/1994 | Imran |
| 5,342,297 A | 8/1994 | Jang |
| 5,342,387 A | 8/1994 | Summers |
| 5,350,395 A | 9/1994 | Yock |
| 5,383,892 A | 1/1995 | Ansel |
| 5,387,235 A | 2/1995 | Chuter |
| 5,395,332 A | 3/1995 | Ressemann et al. |
| 5,395,334 A | 3/1995 | Keith et al. |
| 5,404,887 A | 4/1995 | Prather |
| 5,409,458 A | 4/1995 | Khairkhahan et al. |
| 5,413,581 A | 5/1995 | Goy |
| 5,413,586 A | 5/1995 | Dibie et al. |
| 5,417,208 A | 5/1995 | Winkler |
| 5,425,765 A | 6/1995 | Tiefenbrun et al. |
| 5,437,638 A | 8/1995 | Bowman |
| 5,443,497 A | 8/1995 | Venbrux |
| 5,445,624 A | 8/1995 | Jiminez |
| 5,449,373 A | 9/1995 | Pinchasik et al. |
| 5,449,382 A | 9/1995 | Dayton |
| 5,456,694 A | 10/1995 | Marin et al. |
| 5,456,712 A | 10/1995 | Maginot |
| 5,456,714 A * | 10/1995 | Owen ..................... 623/1.31 |
| 5,458,605 A | 10/1995 | Klemm |
| 5,462,530 A | 10/1995 | Jang |
| 5,476,471 A | 12/1995 | Shifrin et al. |
| 5,489,271 A | 2/1996 | Andersen |
| 5,489,295 A | 2/1996 | Piplani et al. |
| 5,496,292 A | 3/1996 | Burnham |
| 5,505,702 A | 4/1996 | Arney |
| 5,507,768 A | 4/1996 | Lau |
| 5,507,769 A | 4/1996 | Marin et al. |
| 5,514,154 A | 5/1996 | Lau et al. |
| 5,514,178 A | 5/1996 | Torchio |
| 5,522,801 A | 6/1996 | Wang |
| 5,531,788 A | 7/1996 | Dibie et al. |
| 5,545,132 A | 8/1996 | Fagan et al. |
| 5,549,553 A | 8/1996 | Ressemann et al. |
| 5,549,554 A | 8/1996 | Miraki |
| 5,562,620 A | 10/1996 | Klein et al. |
| 5,562,724 A | 10/1996 | Vorwerk et al. |
| 5,562,725 A | 10/1996 | Schmitt et al. |
| 5,562,726 A | 10/1996 | Chuter |
| 5,569,295 A | 10/1996 | Lam |
| 5,571,087 A | 11/1996 | Ressemann et al. |
| 5,575,771 A | 11/1996 | Walinsky |
| 5,575,817 A * | 11/1996 | Martin ..................... 623/1.35 |
| 5,575,818 A | 11/1996 | Pinchuk |
| 5,591,228 A | 1/1997 | Edoga |
| 5,593,442 A | 1/1997 | Klein |
| 5,607,444 A * | 3/1997 | Lam ..................... 606/194 |
| 5,609,605 A | 3/1997 | Marshall et al. |
| 5,609,625 A | 3/1997 | Piplani et al. |
| 5,609,627 A * | 3/1997 | Goicoechea et al. ........ 128/898 |
| 5,609,629 A | 3/1997 | Fearnot et al. |
| 5,613,949 A | 3/1997 | Miraki |
| 5,613,980 A | 3/1997 | Chauhan |
| 5,613,981 A | 3/1997 | Boyle et al. |
| 5,617,878 A * | 4/1997 | Taheri ..................... 128/898 |
| 5,626,600 A | 5/1997 | Horzewski et al. |
| 5,628,788 A | 5/1997 | Pinchuk |
| 5,632,762 A | 5/1997 | Myler |
| 5,632,763 A | 5/1997 | Glastra |
| 5,632,772 A | 5/1997 | Alcime et al. |
| 5,634,902 A | 6/1997 | Johnson et al. |
| 5,639,278 A | 6/1997 | Dereume et al. |
| 5,643,340 A | 7/1997 | Nunokawa |
| 5,653,743 A | 8/1997 | Martin |
| 5,662,614 A | 9/1997 | Edoga |
| 5,669,924 A | 9/1997 | Shaknovich |
| 5,669,932 A | 9/1997 | Fischell et al. |
| 5,676,696 A * | 10/1997 | Marcade ..................... 623/1.35 |
| 5,676,697 A | 10/1997 | McDonald |
| 5,679,400 A | 10/1997 | Tuch |
| 5,683,451 A | 11/1997 | Lenker et al. |
| 5,690,642 A | 11/1997 | Osborne et al. |
| 5,693,084 A | 12/1997 | Chuter |
| 5,693,086 A | 12/1997 | Goicoechea et al. |
| 5,693,088 A | 12/1997 | Lazarus |
| 5,697,971 A | 12/1997 | Fischell et al. |
| 5,707,354 A | 1/1998 | Salmon |
| 5,709,713 A | 1/1998 | Evans et al. |
| 5,716,365 A | 2/1998 | Goicoechea et al. |
| 5,718,683 A | 2/1998 | Ressemann et al. |
| 5,718,724 A | 2/1998 | Goicoechea et al. |
| 5,720,735 A | 2/1998 | Dorros |
| 5,723,004 A | 3/1998 | Dereume et al. |
| 5,724,977 A | 3/1998 | Yock et al. |
| 5,728,158 A | 3/1998 | Lau et al. |
| 5,733,303 A | 3/1998 | Israel et al. |
| 5,735,893 A | 4/1998 | Lau et al. |
| 5,746,766 A | 5/1998 | Edoga |
| 5,749,825 A | 5/1998 | Fischell et al. |
| 5,749,848 A | 5/1998 | Jang et al. |
| 5,755,734 A | 5/1998 | Richter et al. |
| 5,755,735 A * | 5/1998 | Richter et al. ............... 606/194 |
| 5,755,770 A | 5/1998 | Ravenscroft |
| 5,755,771 A | 5/1998 | Penn et al. |
| 5,755,778 A | 5/1998 | Kleshinski |
| 5,762,631 A | 6/1998 | Klein |
| 4,759,748 A | 7/1998 | Reed |
| 5,776,101 A | 7/1998 | Goy |
| 5,776,161 A | 7/1998 | Globerman |
| 5,776,180 A | 7/1998 | Goicoechea et al. |
| 5,782,906 A | 7/1998 | Marshall et al. |
| 5,800,450 A | 9/1998 | Lary et al. |
| 5,800,508 A | 9/1998 | Goicoechea et al. |
| 5,814,061 A | 9/1998 | Osborne et al. |
| 5,817,126 A | 10/1998 | Imran |
| 5,824,008 A | 10/1998 | Bolduc et al. |
| 5,824,036 A | 10/1998 | Lauterjung |
| 5,824,040 A | 10/1998 | Cox et al. |
| 5,824,041 A | 10/1998 | Lenker et al. |
| 5,824,044 A | 10/1998 | Quiachon et al. |
| 5,827,320 A | 10/1998 | Richter et al. |
| 5,833,650 A | 11/1998 | Imran |
| 5,836,966 A | 11/1998 | St. Germain |
| 5,837,008 A | 11/1998 | Berg et al. |

| Patent | Date | Inventor |
|---|---|---|
| 5,843,031 A | 12/1998 | Hermann et al. |
| 5,843,160 A | 12/1998 | Rhodes |
| 5,843,164 A | 12/1998 | Frantzen et al. |
| 5,846,204 A | 12/1998 | Solomon |
| 5,851,210 A | 12/1998 | Torossian |
| 5,851,464 A | 12/1998 | Davila et al. |
| 5,855,600 A | 1/1999 | Alt |
| 5,855,601 A | 1/1999 | Bessler et al. |
| 5,865,178 A | 2/1999 | Yock |
| 5,868,777 A | 2/1999 | Lam |
| 5,871,537 A | 2/1999 | Holman et al. |
| 5,871,936 A | 2/1999 | Lazarus |
| 5,891,133 A | 4/1999 | Murphy-Chutorian |
| 5,897,588 A | 4/1999 | Hull et al. |
| 5,906,640 A | 5/1999 | Penn et al. |
| 5,907,893 A | 6/1999 | Zadno-Azizi et al. |
| 5,913,895 A | 6/1999 | Burpee et al. |
| 5,913,897 A | 6/1999 | Corso, Jr. et al. |
| 5,921,958 A | 7/1999 | Ressemann et al. |
| 5,922,020 A | 7/1999 | Klein et al. |
| 5,928,248 A | 7/1999 | Acker |
| 5,938,682 A | 8/1999 | Hojeibane et al. |
| 5,938,696 A | 8/1999 | Goicoechea et al. |
| 5,948,016 A | 9/1999 | Jang |
| 5,951,599 A | 9/1999 | McCrory |
| 5,961,548 A | 10/1999 | Shmulewitz |
| 5,967,986 A | 10/1999 | Cimochowski et al. |
| 5,972,018 A | 10/1999 | Israel et al. |
| 6,007,517 A | 12/1999 | Anderson |
| 6,013,054 A | 1/2000 | Jiun Yan |
| 6,013,091 A | 1/2000 | Ley et al. |
| 6,017,324 A | 1/2000 | Tu et al. |
| 6,017,363 A | 1/2000 | Hojeibane |
| 6,024,763 A | 2/2000 | Lenker et al. |
| 6,030,414 A | 2/2000 | Taheri |
| 6,033,434 A | 3/2000 | Borghi |
| 6,033,435 A | 3/2000 | Penn et al. |
| 6,036,682 A | 3/2000 | Lange et al. |
| 6,039,749 A | 3/2000 | Marin et al. |
| 6,042,597 A | 3/2000 | Kveen et al. |
| 6,045,557 A | 4/2000 | White et al. |
| 6,048,361 A | 4/2000 | Von Oepen |
| 6,056,775 A | 5/2000 | Borghi et al. |
| 6,059,823 A | 5/2000 | Holman et al. |
| 6,059,824 A | 5/2000 | Taheri |
| 6,066,168 A | 5/2000 | Lau et al. |
| 6,068,655 A | 5/2000 | Sequin et al. |
| 6,071,285 A | 6/2000 | Lashinski et al. |
| 6,086,611 A | 7/2000 | Duffy et al. |
| 6,090,127 A | 7/2000 | Globerman |
| 6,090,128 A | 7/2000 | Douglas |
| 6,096,073 A | 8/2000 | Webster et al. |
| 6,099,497 A | 8/2000 | Adams et al. |
| 6,117,117 A | 9/2000 | Mauch |
| 6,117,156 A | 9/2000 | Richter et al. |
| 6,126,685 A | 10/2000 | Lenker et al. |
| 6,129,738 A | 10/2000 | Lashinski et al. |
| 6,129,754 A | 10/2000 | Kanesaka et al. |
| 6,142,973 A | 11/2000 | Carleton et al. |
| 6,152,945 A | 11/2000 | Bachinski et al. |
| 6,165,195 A | 12/2000 | Wilson et al. |
| 6,165,197 A | 12/2000 | Yock |
| 6,165,214 A | 12/2000 | Lazarus |
| 6,179,867 B1 | 1/2001 | Cox |
| 6,183,506 B1 | 2/2001 | Penn et al. |
| 6,183,509 B1 | 2/2001 | Dibie |
| 6,190,403 B1 | 2/2001 | Fischell et al. |
| 6,193,746 B1 | 2/2001 | Strecker |
| 6,203,569 B1 | 3/2001 | Wijay |
| 6,210,380 B1 | 4/2001 | Mauch |
| 6,210,429 B1 | 4/2001 | Vardi |
| 6,217,527 B1 | 4/2001 | Selmon et al. |
| 6,217,608 B1 | 4/2001 | Penn et al. |
| 6,221,080 B1 | 4/2001 | Power |
| 6,221,090 B1 | 4/2001 | Wilson |
| 6,221,098 B1 | 4/2001 | Wilson et al. |
| 6,231,563 B1 | 5/2001 | White et al. |
| 6,231,598 B1 | 5/2001 | Berry et al. |
| 6,231,600 B1 | 5/2001 | Zhong |
| 6,235,051 B1 | 5/2001 | Murphy |
| 6,241,762 B1 | 6/2001 | Shanley |
| 6,258,073 B1 | 7/2001 | Mauch |
| 6,258,099 B1 | 7/2001 | Mareiro et al. |
| 6,258,116 B1 | 7/2001 | Hojeibane |
| 6,258,121 B1 | 7/2001 | Yang et al. |
| 6,261,273 B1 | 7/2001 | Ruiz |
| 6,261,305 B1 | 7/2001 | Marotta et al. |
| 6,261,319 B1 | 7/2001 | Kveen et al. |
| 6,264,682 B1 | 7/2001 | Wilson et al. |
| 6,273,911 B1 | 8/2001 | Cox et al. |
| 6,273,913 B1 | 8/2001 | Wright et al. |
| 6,287,314 B1 | 9/2001 | Lee et al. |
| 6,290,673 B1 | 9/2001 | Shanley |
| 6,293,967 B1 | 9/2001 | Shanley |
| 6,299,634 B1 | 10/2001 | Bergeron |
| 6,302,906 B1 | 10/2001 | Goicoechea et al. |
| 6,309,412 B1 | 10/2001 | Lau et al. |
| 6,309,414 B1 | 10/2001 | Rolando et al. |
| 6,312,459 B1 | 11/2001 | Huang et al. |
| 6,325,821 B1 | 12/2001 | Gaschino et al. |
| 6,325,826 B1 | 12/2001 | Vardi et al. |
| 6,334,870 B1 | 1/2002 | Her et al. |
| 6,346,089 B1 | 2/2002 | Dibie |
| 6,350,278 B1 | 2/2002 | Lenker et al. |
| 6,355,060 B1 | 3/2002 | Lenker et al. |
| 6,361,544 B1 | 3/2002 | Wilson et al. |
| 6,361,555 B1 | 3/2002 | Wilson |
| 6,383,215 B1 | 5/2002 | Sass |
| 6,387,120 B2 | 5/2002 | Wilson et al. |
| 6,395,018 B1 | 5/2002 | Castaneda |
| 6,398,792 B1 | 6/2002 | O'Connor |
| 6,398,804 B1 | 6/2002 | Spielberg |
| 6,428,570 B1 | 8/2002 | Globerman |
| 6,432,133 B1 | 8/2002 | Lau et al. |
| 6,436,104 B2 | 8/2002 | Hojeibane |
| 6,436,134 B2 | 8/2002 | Richter et al. |
| 6,478,816 B1 | 11/2002 | Kveen et al. |
| 6,482,211 B1 | 11/2002 | Choi |
| 6,485,511 B2 | 11/2002 | Lau et al. |
| 6,494,905 B1 | 12/2002 | Zedler et al. |
| 6,511,504 B1 | 1/2003 | Lau et al. |
| 6,511,505 B2 | 1/2003 | Cox et al. |
| 6,520,988 B1 | 2/2003 | Colombo et al. |
| 6,527,799 B2 | 3/2003 | Shanley |
| 6,540,719 B2 | 4/2003 | Bigus et al. |
| 6,540,779 B2 | 4/2003 | Richter et al. |
| 6,572,647 B1 | 6/2003 | Supper |
| 6,579,309 B1 | 6/2003 | Loos et al. |
| 6,579,312 B2 | 6/2003 | Wilson et al. |
| 6,582,394 B1 | 6/2003 | Reiss et al. |
| 6,582,459 B1 | 6/2003 | Lau et al. |
| 6,596,020 B2 * | 7/2003 | Vardi et al. ................ 623/1.11 |
| 6,596,022 B2 | 7/2003 | Lau et al. |
| 6,599,316 B2 | 7/2003 | Vardi et al. |
| 6,645,241 B1 | 11/2003 | Strecker |
| 6,659,957 B1 * | 12/2003 | Vardi et al. ................ 600/467 |
| 6,682,536 B2 * | 1/2004 | Vardi et al. ................ 606/108 |
| 6,689,156 B1 | 2/2004 | Davidson et al. |
| 6,692,483 B2 | 2/2004 | Vardi et al. |
| 6,706,062 B2 | 3/2004 | Vardi et al. |

* cited by examiner

METHOD FOR EMPLOYING AN EXTENDIBLE STENT APPARATUS

This application is a continuation of U.S. Ser. No. 08/935,363 filed Sep. 23, 1997 (now abandoned), which is a divisional application of U.S. Ser. No. 08/744,002 filed Nov. 4, 1996 (now abandoned).

BACKGROUND

A type of endoprosthesis device, commonly referred to as a stent, is placed or implanted within a vein, artery or other tubular body organ for treating occlusions, stenoses, or aneurysms of the vessel. These stent devices are implanted within tubular vessels to reinforce collapsing, partially occluded, weakened, or abnormally dilated segments of the vessel wall. Stents have been used to treat dissections in blood vessel walls caused by balloon angioplasty of the coronary arteries as well as peripheral arteries and to improve angioplasty results by preventing elastic recoil and remodeling of the vessel wall.

Stents also have been successfully implanted in the urinary tract, the bile duct, the esophagus and the tracheobronchial tree to reinforce those body organs. Two randomized multicenter trials have recently shown a lower restenosis rate in stent treated coronary arteries compared with balloon angioplasty alone (Serruys P W et. al. New England Journal of Medicine 331: 489–495, 1994, Fischman D L et. al. New England Journal of Medicine 331: 496–501, 1994).

One of the drawbacks of conventional stents is that they are produced in a straight tubular configuration. The use of such stents to treat disease at or near a branch or bifurcation of a vessel runs the risk of compromising the degree of patency of the primary vessel and/or its branches or bifurcation and also limits the ability to insert a second stent into the side branch if the angioplasty result is suboptimal. This may occur as a result of several mechanisms such as displacing diseased tissue or plaque shifting, vessel spasm, dissection with or without intimal flaps, thrombosis, and embolism.

The risk of branch compromise is increased in two anatomical situations. First the side branch can be compromised when there is a stenosis in the origin of the side branch. Second, when there is an eccentric lesion at the bifurcation site, asymmetric expansion can cause either plaque shifting or dissection at the side branch origin. There are reports of attempting to solve this problem by inserting a balloon into the side branch through the stent struts; however, this technique carries the risk of balloon entrapment and other major complications (Nakamura, S. et al., Catheterization and Cardiovascular Diagnosis 34: 353–361 (1995)). Moreover, adequate dilatation of the side branch is limited by elastic recoil of the origin of the side branch. In addition, the stent may pose a limitation to blood flow and may limit access to the side branch. The term "stent jail" is often used to describe this concept. In this regard, the tubular slotted hinged design of the Palmaz-Schatz intracoronary stent, in particular, is felt to be unfavorable for lesions with a large side branch and it is believed to pose a higher risk of side branch vessel entrapment where the stent prevents or limits access to the side branch. Id.

One common procedure for implanting the endoprosthesis or stent is to first open the region of the vessel with a balloon catheter and then place the stent in a position that bridges the treated portion of the vessel in order to prevent elastic recoil and restenosis of that segment. The angioplasty of the bifurcation lesion has traditionally been performed using the kissing balloon technique where two guidewires and two balloons are inserted, one into the main branch and the other into the side branch. Stent placement in this situation will require the removal of the guidewire from the side branch and reinsertion of the guidewire via the stent struts and insertion of a balloon through the struts of the stent. The removal of the guidewire poses the risk of occlusion of the side branch during the deployment of the stent in the main branch.

Prior art patents refer to the construction and design of both the stent as well as the apparatus for positioning the stent within the vessel. One representative patent to Chaudhury, U.S. Pat. No. 4,140,126, discloses a technique for positioning an elongated cylindrical stent at a region of an aneurysm to avoid catastrophic failure of the blood vessel wall. The '126 patent discloses a cylinder that expands to its implanted configuration after insertion with the aid of a catheter. Dotter, U.S. Pat. No. 4,503,569, discloses a spring stent which expands to an implanted configuration with a change in temperature. The spring stent is implanted in a coiled orientation and is then heated to cause the spring to expand. Palmaz, U.S. Pat. No. 4,733,665, discloses a number of stent configurations for implantation with the aid of a catheter. The catheter includes a mechanism for mounting and retaining the vascular prosthesis or stent, preferably on an inflatable portion of the catheter. The stents are implanted while imaged on a monitor. Once the stent is properly positioned, the catheter is expanded and the stent separated from the catheter body. The catheter can then be withdrawn from the subject, leaving the stent in place within the blood vessel. Palmaz, U.S. Pat. No. 4,739,762, discloses an expandable intraluminal graft. Schjeldahl et. al., U.S. Pat. No. 4,413,989, discloses a variety of balloon catheter constructions. Maginot, U.S. Pat. No. 5,456,712 and Maginot, U.S. Pat. No. 5,304,220 disclose graft and stent assembly and method of implantation where a stent is used to reinforce a graft surgically inserted into a blood vessel in order to bypass an occlusion. However, none of these patents relate to the treatment of bifurcation lesions, or disclose a bifurcating stent apparatus and method for deploying the same.

Taheri, U.S. Pat. No. 4,872,874, Piplani et. al., U.S. Pat. No. 5,489,295, and Marin et al., U.S. Pat. No. 5,507,769, disclose bifurcating graft material which may be implanted with stents. However, there is no mention of bifurcation of the stent, and the stent is used only to anchor the graft into the vessel wall. It does not reinforce the vessel wall, nor does it prevent restenosis after angioplasty.

MacGregor, U.S. Pat. No. 4,994,071, discloses a hinged bifurcating stent. In the '071 patent, in contrast to the present invention, there is a main stent with two additional stents attached at one end, creating a single unit with a bifurcation. The two additional stents are permanently attached and cannot be removed from the main stent. Thus, this invention may not be used in non-bifurcation vessels. In addition, studies with hinge-containing stents have shown that there is a high incidence of restenosis (tissue growth) at the hinge point that may cause narrowing or total occlusion of the vessel and thus compromise blood flow. Furthermore, this design has a relatively large size which makes insertion into the vessel difficult. Also, by having the two additional stents connected to the main stent, tracking into a wide-angle side branch may be difficult and may carry the risk of dissection of the vessel wall. Furthermore, once the device of the '071 patent is implanted, it is impossible to exchange the side branch stent should the need for a different stent size arise.

In general, when treating a bifurcation lesion using commercially available stents, great care should be taken to cover the origin of the branch because if left uncovered, this area is prone to restenosis. In order to cover the branch origin, conventional stents must either protrude into the lumen of the main artery or vessel from the branch (which may causes thrombosis [clotting of blood], again compromising blood flow), or they must be placed entirely within the branch, and will generally not cover the origin of the bifurcation. Another frequent complication experienced with the stenting of bifurcations include narrowing or occlusion of the origin of a side branch spanned by a stent placed in the main branch. Lastly, placement of a stent into a main vessel where the stent partially or completely extends across the opening of a branch may make future access into such branch vessels difficult if not impossible.

In addition, conventional stent technology is inadequate as a means of treating ostial lesions. Ostial lesions are lesions at the origin of a vessel. For example, ostial lesions may form in renal arteries, which are side branches extending from the aorta. Ostial lesions are prone to restenosis due to elastic recoil of the main vessel, such as the aorta. Therefore, the stent cover must include the thickness of the wall of the main vessel. This is extremely difficult to accomplish without protrusion of the stent into the main vessel.

Lastly, conventional stents are difficult to visualize during and after deployment. While some prior art balloon catheters are "marked" at the proximal and distal ends of the balloon with imageable patches, no FDA-approved stents are currently available which are themselves imageable through currently known imaging procedures used when inserting the stents into a vessel.

Accordingly, there is a need for an improved stent apparatus and method for deploying the same which 1) may be used to effectively treat bifurcation lesions which reduces the risk of restenosis or occlusion of the side branch and which completely covers bifurcation lesions with the stent apparatus, 2) may be used to treat lesions in one branch of a bifurcation while preserving access to the other branch for future treatment, 3) may be used to treat ostial lesions, 4) allows for differential sizing of the stents in a bifurcated stent apparatus even after the main stent is implanted, and which 5) may be readily visualized by current or future visualization techniques.

SUMMARY OF THE INVENTION

The present invention concerns a novel extendable stent apparatuses and method for deploying the same. More particularly, the invention concerns a stent apparatus comprising an extendable stent which is suitable for treating bifurcation lesions, and which may also be used to treat lesions at the origin of a blood vessel or other organ. As used herein, the term "vessel" means any tubular tissue, and is not limited to vessels of the vascular system. Devices constructed in accordance with the invention include, singularly or in combination, a flared stent comprising a compressible flared portion at its proximal end, which flared portion may comprise hooks, compressible mesh or any other means of creating such a flared portion at the proximal end of the stent, and a main stent comprising at least one substantially circular opening located between its proximal and distal ends. For ease of visualization, both the flared stent and the main stent may be comprised of materials which are imageable, or the stents of the invention may be "marked" at the ends with an imageable substance and the main stent may also be marked at any opening. At least one flared stent may be extended through at least one opening of the main stent into at least one branch vessel for treating bifurcated or branched lesions, or the stents of the invention may be inserted individually for the treatment of ostial lesions, or lesions near bifurcations requiring a stent in either the main or the branch vessel with unobstructed access to the unstented vessel in the bifurcation. The methods of the invention comprises a two-step process used to deploy both the main and the flared stent in a bifurcated vessel, or to deploy the main stent only within a bifurcated vessel.

The stent apparatus of the invention may be constructed from any non-immunoreactive material that allows the apparatus to be expanded from an initial shape to a shape which conforms to the shape of the vessel or vessels into which the apparatus is inserted, including but not limited to any of the materials disclosed in the prior art stents, which are incorporated herein by reference. It is hypothesized that the stent apparatuses of the invention may further be constructed of a substance which is observable by imaging methods including but not limited to magnetic resonance, ultrasound, radio-opaque or contrast-dye, or may be marked at certain points including but not limited to the ends and around any opening or flared portion in a stent of the invention, with a material which is discernable by imaging methods as described above.

A stent constructed in accordance with the invention is suitable for implantation into any vessel in the body, including but not limited to vessels in the cardiac system, the peripheral vascular system, the carotid and intracranial vessels, the venous system, the renal system, the biliary system, the gastrointestinal system, the tracheobronchial system, the biliary system and the genitourinary system.

The stents of the invention are deployed utilizing a set of guidewires and catheters, which are then withdrawn from the subject following deployment of the stents. The stents of the invention may be self-expanding to conform to the shape of the subject vessel, or they may be expanded utilizing balloon catheters, or by any method currently known or developed in the future which is effective for expanding the stents of the invention. The flared stent of the invention is constructed such that the flared portion is confined along the wall of the flared stent by a sheath running parallel to the longitudinal axis of the flared stent until deployment, during which the sheath is removed and the flared portion is expanded into a configuration extending radially, at least in part, from the longitudinal axis of the flared stent.

Thus, it is an object of the present invention to provide a double-stent apparatus which makes it possible to completely cover the origin of a bifurcation lesion with a stent apparatus.

Another object of the invention is to provide a single-stent apparatus and method for deploying the same which may be used to treat only one branch of a bifurcation lesion but which will facilitate future treatment of the corresponding branch.

Yet another object of the invention is to provide a single-stent apparatus which is effective in treating ostial lesions.

A further object of the invention is to provide a method for insertion of the extendable double-stent apparatus into both the main and branch vessels of a bifurcation lesion.

Additionally, it is an object of the invention to provide a stent apparatus which is imageable during and after insertion.

These objects and other object advantages and features of the invention will become better understood from the detailed description of the invention and the accompanying drawings.

BRIEF DESCRIPTION OF THE DRAWINGS

FIG. 6 is a schematic depiction of the method of the invention.

Figure 1:
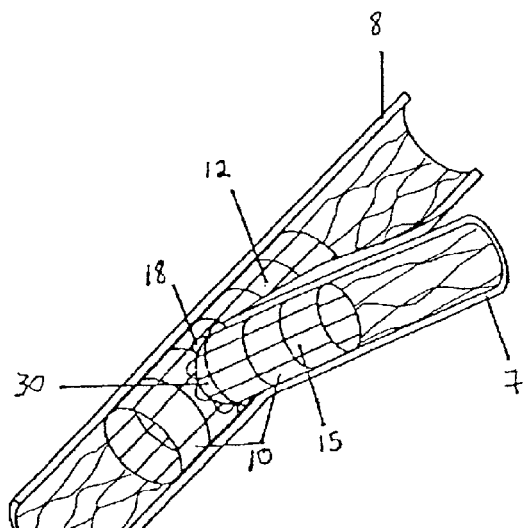
FIG. 1 is a schematic depiction of the double-stent apparatus of the present invention in which both the main stent and the flared stent are fully dilated.

The rectilinear matrices shown in the drawings are intended to show the shapes of the surfaces only, and do not illustrate the actual surface patterns or appearances of the stent apparatuses of the invention.

DESCRIPTION OF THE PREFERRED EMBODIMENTS

The bifurcating double-stent apparatus 10 of the present invention comprises a generally cylindrical main stent 12 and a generally cylindrical flared stent 15, which are shown as fully dilated in a subject main vessel 8 and a subject branch vessel 7, as illustrated in FIG. 1.

Figure 2:
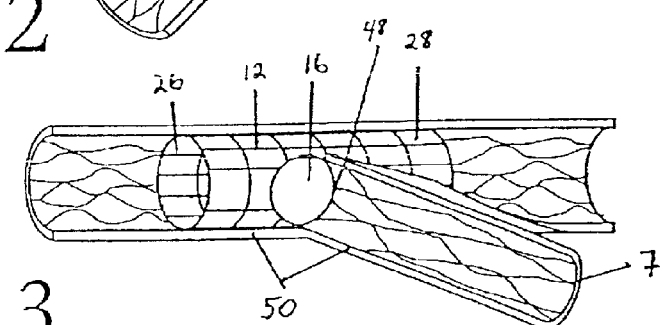
FIG. 2 is a schematic depiction of the main stent of the apparatus of the invention as deployed, without placement of the flared stent.

The main stent 12 contains at least one generally circular opening 16 located between the proximal end 26 and the distal end 28 of the main stent 12 (FIG. 2), which opening is positioned over the opening 48 of a branch vessel in a vessel bifurcation 50, as shown in FIG. 2. The ends of the stent 12 and the opening are imaged during imaging procedures by placing markers 56 around the edges of the opening 16 in the main stent 12 and at the proximal end 26 and distal end 28 of the main stent, as illustrated in FIG. 4.

Figure 3:
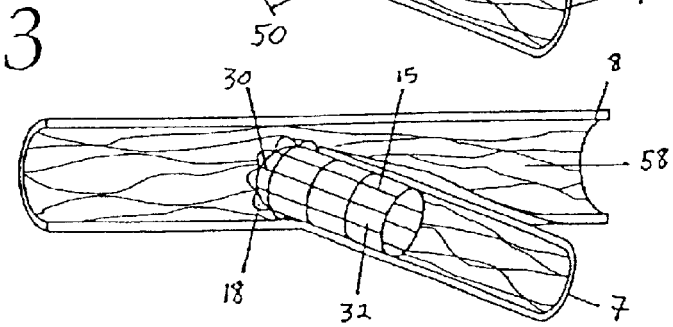
FIG. 3 is a schematic depiction of the flared stent of the apparatus as deployed, without the main stent.

The flared stent apparatus 15 of the present invention comprises a generally cylindrical flared stent comprising a proximal end 30 and a distal end 32, as shown in FIG. 3. The proximal end 30 comprises a flared portion, illustrated here as extended loops 18, which flared portion, when dilated, is positioned within the lumen 58 of the main vessel 8 (FIG. 3). The ends of the flared stent 15 and the flared portion 18 are imaged during imaging procedures by placing markers 56 around the flared portion 18 and at the proximal end 30 and distal end 32 of the flared stent, as illustrated in FIG. 5.

Figure 4:
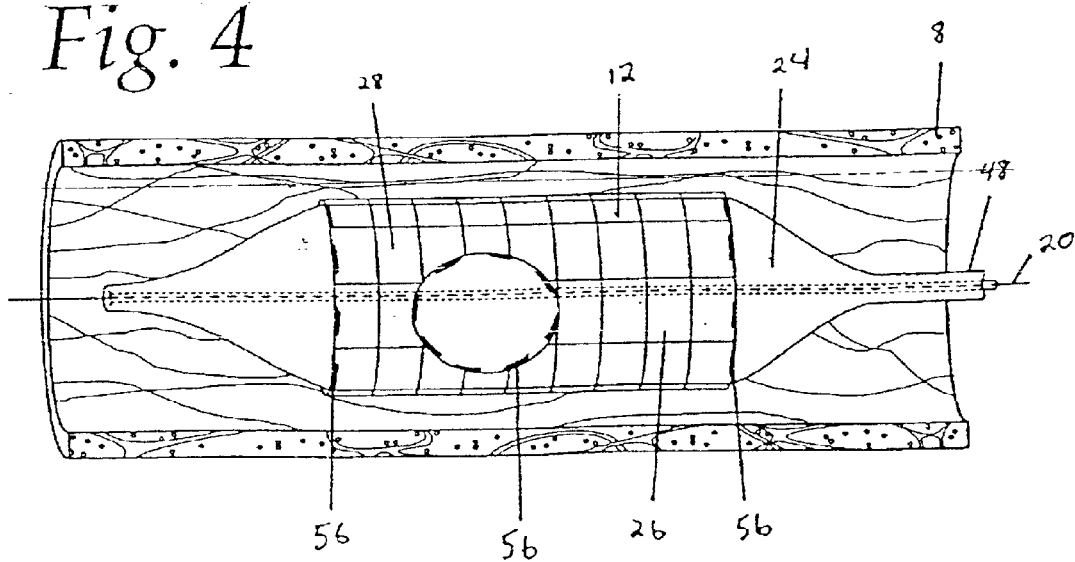
FIG. 4 is a schematic depiction of the main stent of the apparatus deployed within a subject vessel.

As shown in the embodiment of the invention illustrated in FIG. 4, a guidewire 20 is inserted into the vessel 8 prior to insertion of the main stent 12, and is used to guide the main stent 12 into position within the vessel 8. Prior to insertion and dilation, the main stent 12 is disposed around the distal end of a catheter 48 which may include an inflatable balloon 24. The main stent/catheter apparatus is then threaded onto the main guidewire 20 and into the vessel 8. The main stent 12 is dilated by inflation of the balloon 24 until it expands the walls of the vessel 8, and is thus affixed into place.

Figure 5:
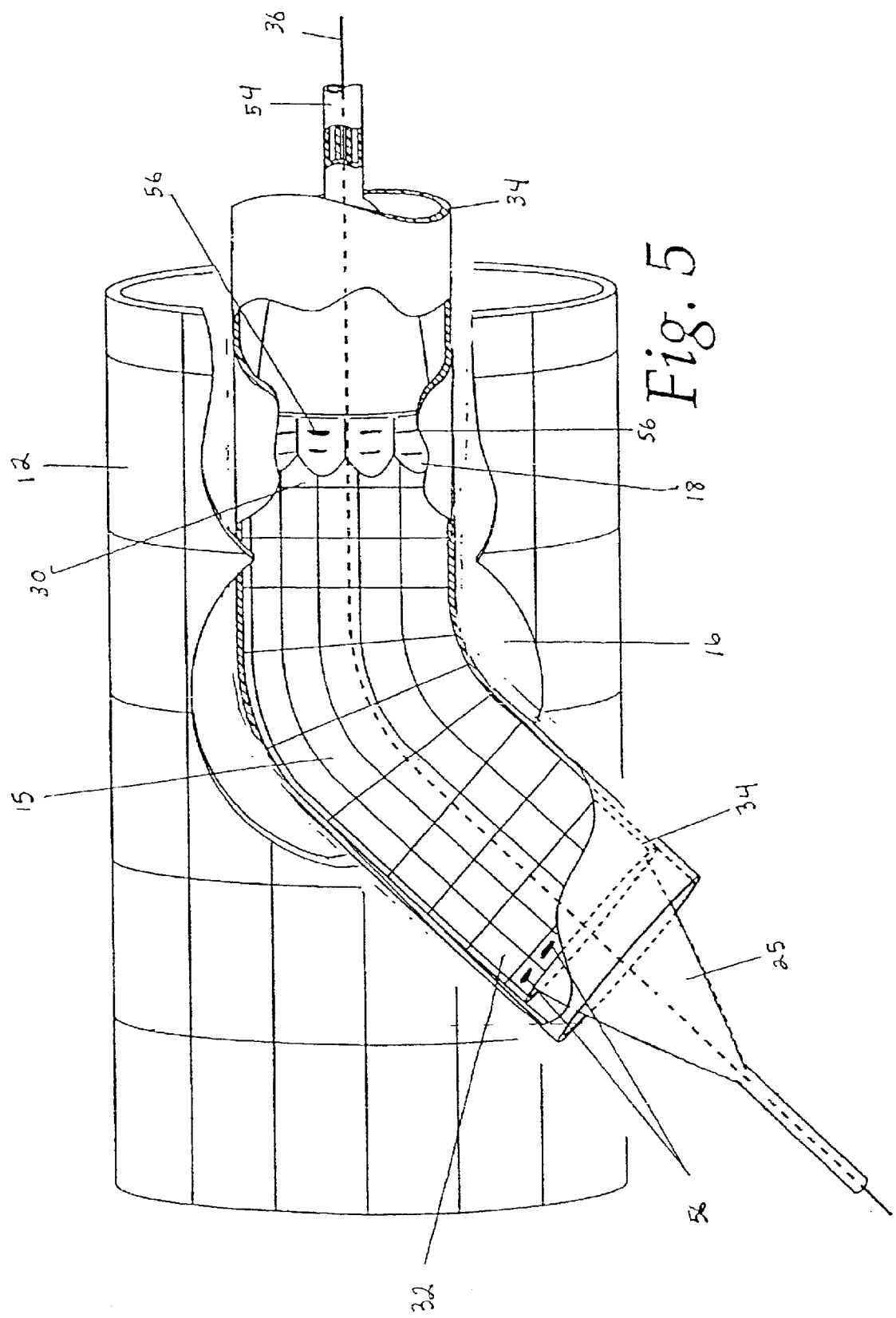
FIG. 5 is a schematic depiction of the double-stent bifurcating stent apparatus, where the main stent is deployed and showing the placement of the flared stent apparatus prior to full deployment of the flared stent.

As shown in the embodiment of the invention illustrated in FIG. 5, prior to insertion of the flared stent 15, a guidewire 36 and a stabilizing catheter 44 are inserted through the opening 16 in the main stent 12, and into a branch vessel. The stabilizing catheter 44 is used to place the opening in the main stent 12 over the opening 16 in the bifurcation. The guidewire 36 is used to guide the flared stent 15 into position within a vessel. During insertion and prior to dilation, the flared stent 15 is disposed around the distal end of a branch catheter 54 which may include an inflatable balloon 25, and the flared portion 18 of the flared stent 15 is held in a compressed position by a protective sheath 34.

In the bifurcating double-stent apparatus 10 of the invention, once the main stent 12 is dilated and the stabilizing catheter 44 is removed, the flared stent 15 is inserted over the branch guidewire 36 and through the opening 16 of the main stent 12 substantially as shown in FIG. 5, and affixed in place by the expansion of the flared portion 18 positioned at the proximal end 30 of the flared stent, as shown in FIGS. 1 and 5. The angle at which the flared stent 15 is affixed depends upon the vessel structure into which the bifurcating stent apparatus 10 is inserted (FIG. 1).

Figure 6A:
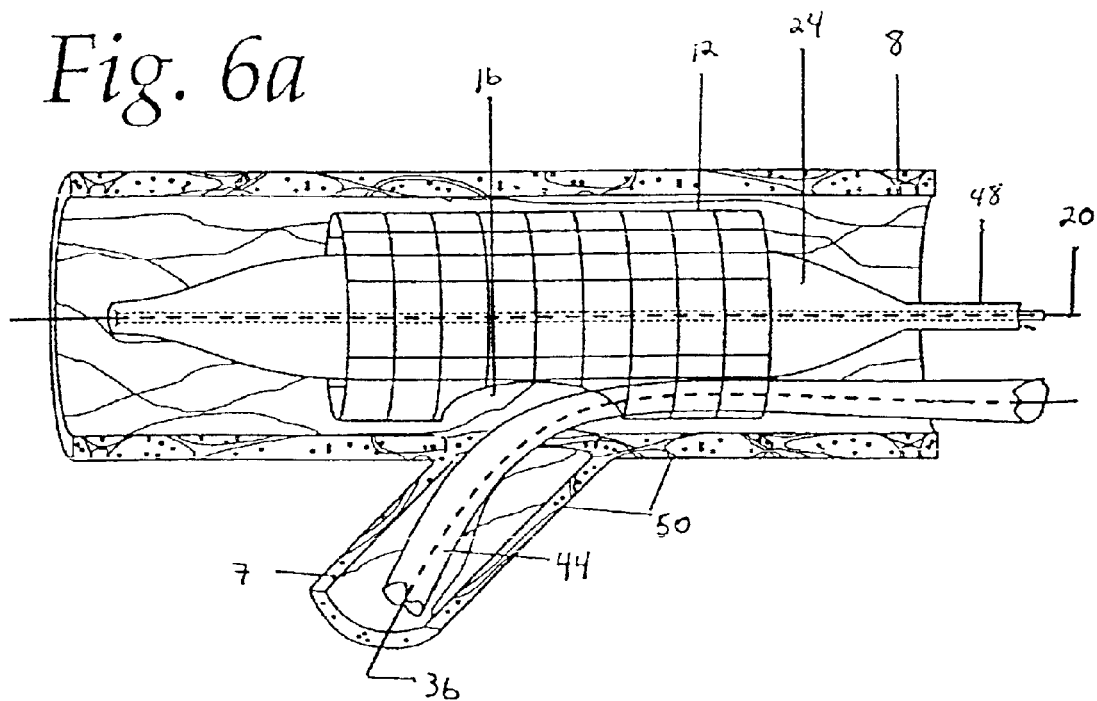
FIG. 6a depicts initial placement of the main stent of the bifurcating stent apparatus into the vessel, along with the insertion of guidewire and stabilizing catheter for placement of the flared stent into the branch vessel of the subject.

The inventive two-stage method for implanting the novel bifurcating double-stent apparatus 10 begins with insertion of the main guidewire 20 into the subject main vessel 8 and across the bifurcation 50. Once the main guidewire 20 is in position in the main vessel 8, the main stent 12 is mounted around a catheter 48 (which may also comprise a balloon 24), and the catheter 48 and stent 12 are inserted into the main vessel 8. The stent 12 is positioned so that the opening 16 is directly over the bifurcation point 50 in the subject vessel (FIG. 6a). In order to aid such positioning, a side branch guidewire 36 and a stabilizing catheter 44 (as depicted in FIGS. 5 and 6) are also inserted through the opening 16 of the main stent 12 and into the branch vessel 7 (FIG. 6a).

In an alternative embodiment of the method of the invention, the main stent 12, the catheters 44 and 48 and the side branch guidewire 36 may be assembled in advance of insertion (with the stabilizing catheter 44 and the side branch guidewire positioned through the opening 16 of the main stent) into the subject, and then inserted into the bifurcation point 50 in the main vessel 8 simultaneously, after which the side branch guidewire 36 and the stabilizing catheter 44 are threaded into the branch vessel 7 in order to properly align the opening 16 in the main stent 12 (FIG. 6a).

Figure 6B:
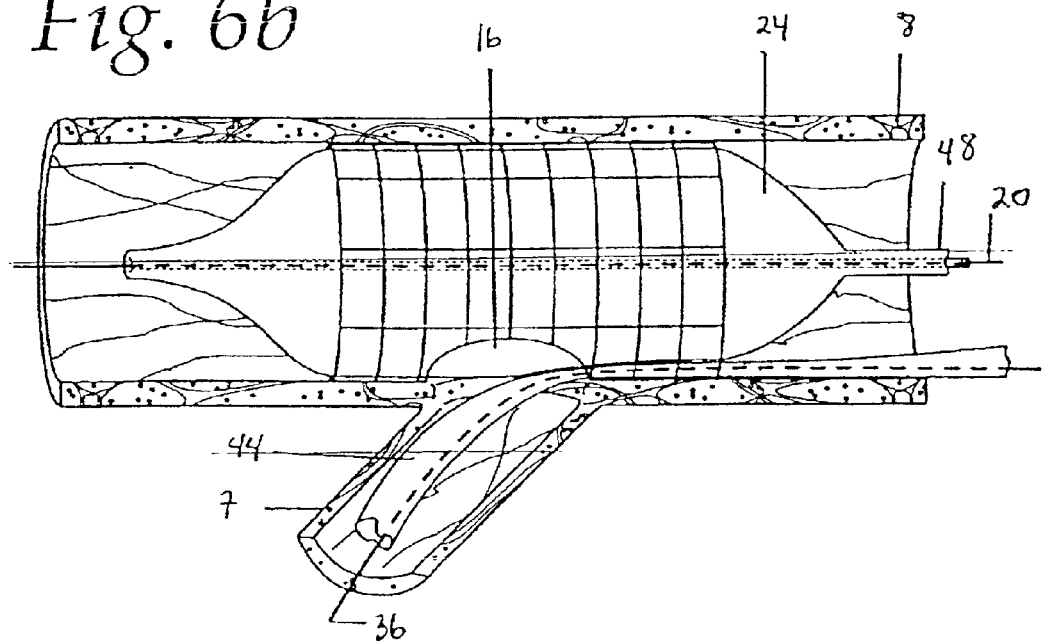
FIG. 6b is a schematic depiction of the step of inflating the main stent of the invention.

To affix the main stent 12 in the desired position within the vessel 8, the stent 12 may be dilated by inflating the balloon 24 until the main stent 12 is in contact with the walls of the vessel 8 (FIG. 6b). Once the main stent 12 is dilated, the catheters 44 and 48 are withdrawn, leaving the fully positioned main stent 12 and the main guidewire 20 in the main subject vessel, and the side branch guidewire 36 in the subject branch vessel (FIG. 6c).

Figure 6C:
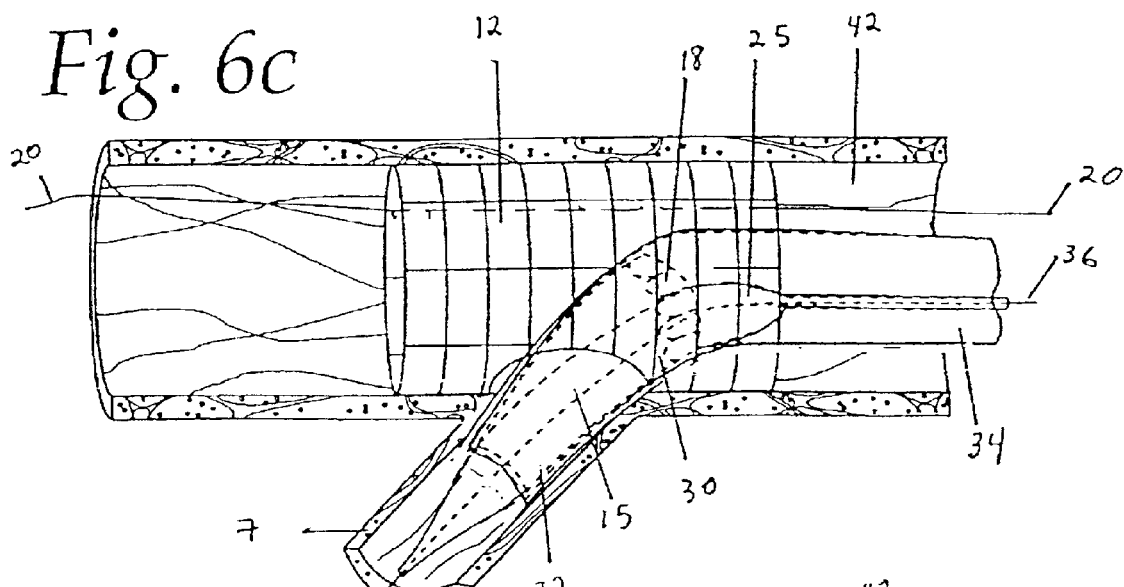
FIG. 6c is a schematic depiction of the deployment of the flared stent over the side branch guidewire, through an opening in the main stent and into the branch vessel of the subject.
Figure 6D:
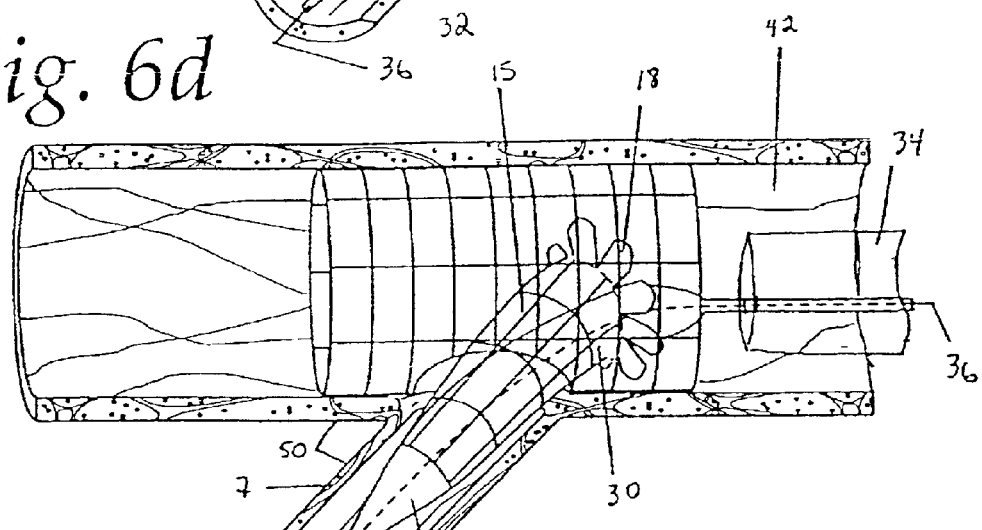
FIG. 6d is a schematic depiction of the removal of the protective sheath of the flared stent, allowing for full expansion of the flared portion prior to placement and deployment.
Figure 6E:
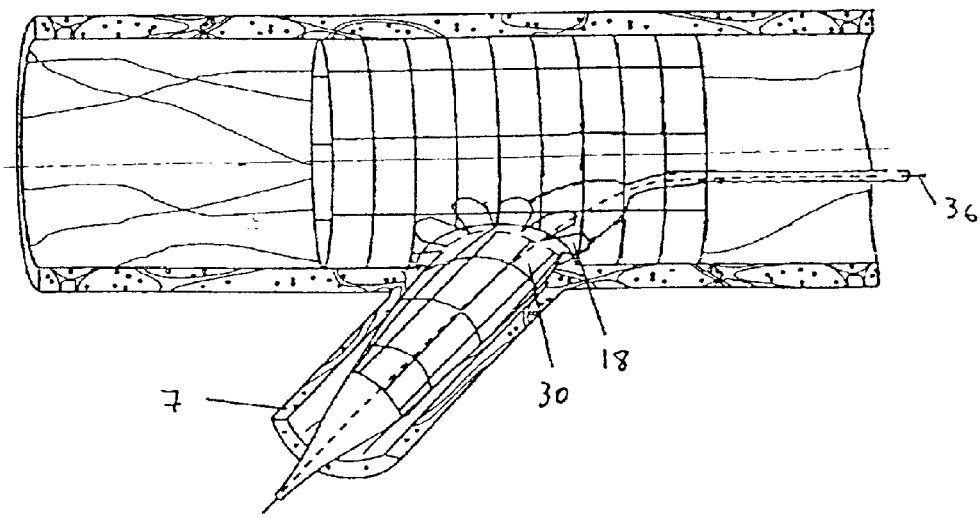
FIG. 6e is a schematic depiction of the fully extended flared stent positioned into the branch by the catheter, but prior to full deployment.
Figure 6F:
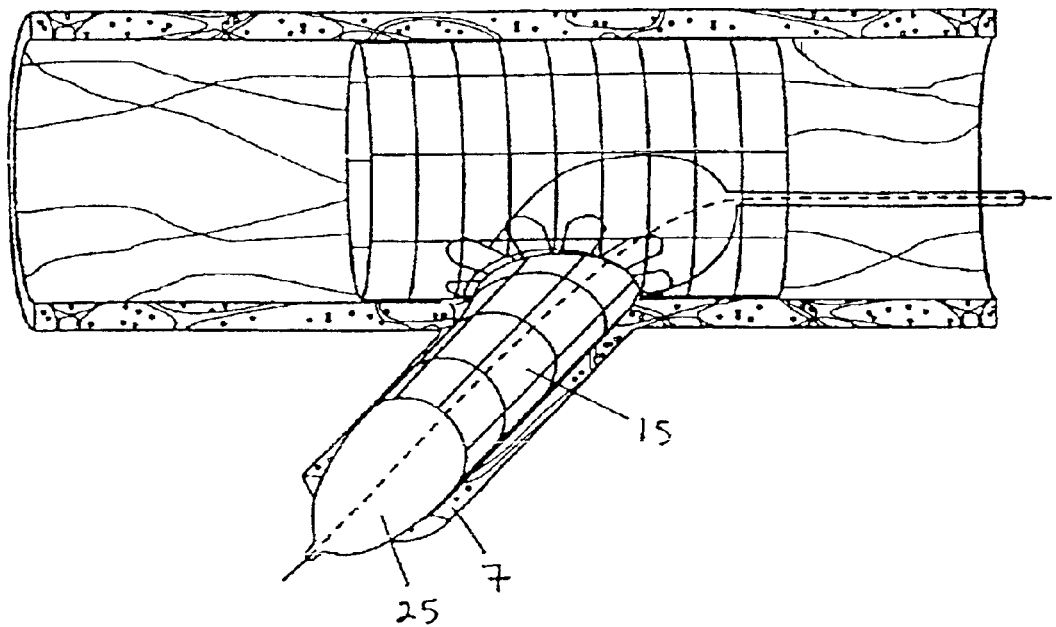
FIG. 6f is a schematic depiction of the fully dilated main stent and the fully positioned flared stent, where the flared stent is being dilated by inflation of the balloon.
Figure 6G:
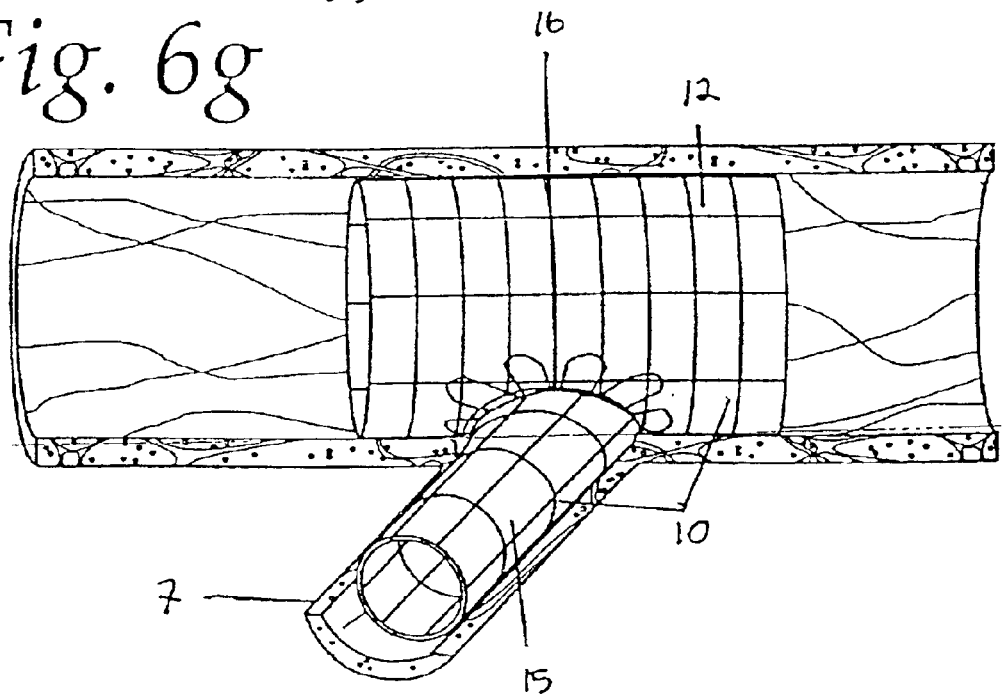
FIG. 6g is a schematic depiction of the fully dilated bifurcating double stent of the invention, positioned into the bifurcation in a subject vessel.

In the second stage of the method of deploying the bifurcating double-stent of the invention, the flared stent catheter 54, containing the compressed flared stent 15 in a protective sheath 34 and which may further contain a balloon 25 disposed around the flared stent catheter 54 and inside the compressed flared stent 15, is inserted into the subject branch vessel 7 around the side branch guidewire 36 as shown in FIG. 6c. The compressed flared stent 15 is initially positioned so that the compressed proximal end 30 of the flared stent extends into the lumen 42 of the main stent 12 to facilitate full expansion of the flared portion 18 after withdrawal of the protective sheath 34, prior to the final positioning of the flared stent 15 into the branch of the bifurcation (FIG. 6c). The distal end 32 of the flared stent is initially positioned within the branch vessel 7 (FIG. 6c). After the proximal end 30 of the compressed flared stent is properly placed within the lumen 42 of the main stent, the protective sheath 34 is withdrawn from the vessel 8, and the flared portion 18 of the flared stent 15 is decompressed to extend radially, at least in part, to the longitudinal axis of the flared stent 15, as shown in FIG. 6d. After the flared portion 18 of the flared stent 15 is in its flared configuration (as shown in FIG. 6d), the flared stent 15 is advanced into the side branch 7 at its proximal end 30 until at least a portion of flared portion 18 of the flared sheath 15 contacts at least a portion of an edge of the opening 16 of the main stent 12, as shown in FIG. 6e. In this example, a balloon 25 is inflated in order to dilate the flared stent 15 to bring the walls of the flared stent 15 into contact with the walls of the branch vessel 7, as shown in FIG. 6f. All remaining catheters and guidewires are then withdrawn from the subject, leaving the fully deployed bifurcating double-stent apparatus of the invention 10, comprising the main stent 12 with at least one opening 16, and the flared stent 15 positioned through the opening 16 into the branch vessel 7, as shown in FIG. 6g.

When treating ostial lesions, the flared stent 15 alone is used, and is positioned utilizing catheters and guidewires as described above, except that a stabilizing catheter is not used, and the flared portion 18 of the flared stent is positioned at the ostium of a vessel, instead of into a side branch through the an opening 16 in a main branch. After the flared stent 15 is positioned near the ostium of a subject vessel, the protective sheath 34 is retracted in order to allow the flared portion to fully expanded and the flared stent 15 is further advanced with the proximal end of the catheter until the unfolded hooks 18 are in contact with the walls of the subject vessel.

All the stents of the invention may be deployed using the methods of the invention without resort to a balloon catheter. For example, a self-expanding compressed stent contained within a protective sheath could be self-dilated by retraction of a protective sheath. Other methods of dilation of the stents of the invention may exist, or may become available in the future, and such methods are contemplated as being within the scope of this invention. While this example used self-unfolding loops to demonstrate one means of creating a flared portion, any other means of creating a flare, such as but not limited to creating a roll in the stent material which is then compressed, is contemplated as within the scope of this invention.

It is the intent that the invention include all modifications and alterations from the disclosed embodiments that fall within the scope of the claims of the invention.

We claim:

1. A method of deploying a stent apparatus in a bifurcated vessel, the bifurcated vessel comprises a main vessel having an ostium leading into a branch vessel, the method comprising:

providing a main stent, which has a proximal end, a distal end and a side opening between the proximal and distal ends, on a first catheter, wherein the main stent comprises a tubular member having a substantially constant diameter along its longitudinal axis;

advancing said first catheter via a first guidewire into the main vessel so that said side opening is substantially aligned with the ostium leading into the branch vessel;

expanding said main stent in its position;

removing said first catheter;

advancing via a second guidewire disposed in the branch vessel a second catheter, having a flareable stent in a state of compression, wherein said flareable stent comprises a proximal end and a distal end, and wherein said proximal end comprises a flareable portion initially in an unflared configuration;

positioning said second catheter within the branch vessel so that said proximal end of said flareable stent extends into the main vessel;

positioning said flareable stent with respect to the ostium by at least allowing said flareable portion in said unflared configuration to be flared radially; and expanding said flareable stent in the branch vessel to deploy said flareable stent in its position within the branch vessel.

2. The method of claim 1, wherein allowing said flareable portion to be flared is accomplished by removal of an outer sheath.

3. The method of claim 1, wherein said second guidewire is introduced after said main stent has been expanded within the main vessel.

4. The method of claim 1, wherein said second guidewire is introduced simultaneously with said first catheter and said main stent.

5. The method of claim 1, wherein expanding of said main stent and said flareable stent are performed by balloon catheterization.

6. The method of claim 1, wherein advancing said first catheter is done using radiopaque markers.

7. The method of claim 1, wherein said flareable stent includes radiopaque markers.

* * * * *

UNITED STATES PATENT AND TRADEMARK OFFICE
CERTIFICATE OF CORRECTION

PATENT NO. : 6,962,602 B2  Page 1 of 1
APPLICATION NO. : 10/050524
DATED : November 8, 2005
INVENTOR(S) : Gil M. Vardi and Charles J. Davidson It is certified that error appears in the above-identified patent and that said Letters Patent is hereby corrected as shown below:

On the title page item (73), add:

Assignee:  Advanced Stent Technologies, LLC, Pleasanton, CA (US)

Signed and Sealed this

First Day of May, 2007

JON W. DUDAS
*Director of the United States Patent and Trademark Office*